United States Patent [19]

Marko

[11] 4,403,082
[45] Sep. 6, 1983

[54] SILOXANE CROSSLINKERS

[75] Inventor: Ollie W. Marko, Carrollton, Ky.

[73] Assignee: Dow Corning Corporation, Midland, Mich.

[21] Appl. No.: 405,656

[22] Filed: Aug. 5, 1982

Related U.S. Application Data

[62] Division of Ser. No. 295,411, Aug. 24, 1981, Pat. No. 4,360,687.

[51] Int. Cl.³ .............................................. C08G 77/06
[52] U.S. Cl. ...................................... 528/15; 528/31; 528/32; 525/478
[58] Field of Search ............................ 528/15, 31, 32; 525/478

[56] References Cited

U.S. PATENT DOCUMENTS

| | | | |
|---|---|---|---|
| 2,550,205 | 4/1951 | Speier | 556/440 |
| 2,770,633 | 11/1956 | Sommer | 556/440 |
| 2,922,806 | 1/1960 | Merker | 556/440 |
| 3,654,332 | 4/1972 | Berger | 556/440 |
| 3,830,744 | 8/1974 | Traver | 556/440 |
| 4,360,687 | 11/1982 | Marko | 528/41 |

FOREIGN PATENT DOCUMENTS 2229294 1/1973 Fed. Rep. of Germany .

*Primary Examiner*—Melvyn L. Marquis
*Attorney, Agent, or Firm*—Neal O. Willmann

[57] ABSTRACT

Compounds useful as crosslinkers and having the formula:

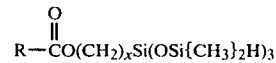

wherein R is selected from the group consisting of alkyl having 1 to 4 carbon atoms, trifluoromethyl and phenyl and x is an integer of 2 to 4, can be used to cure polyorganosiloxanes.

4 Claims, No Drawings

SILOXANE CROSSLINKERS

This application is a division of application Ser. No. 295,411 filed Aug. 24, 1981, now U.S. Pat. No. 4,360,687.

BACKGROUND OF THE INVENTION

1. Field of the Invention

This disclosure relates to novel compounds that can be used as crosslinkers to cure polyorganosiloxanes.

2. Description of the Prior Art

The reaction between a polyorganosiloxane containing aliphatic unsaturation and an organohydrogensiloxane in the presence of a catalyst is well known in the art. The reaction essentially involves the establishment of a new Si—C bond according to the following abbreviated equation:

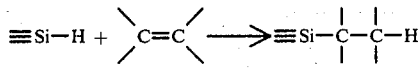

and is elaborated in U.S. Pat. No. 2,823,218, issued Feb. 11, 1958, to Speier et al.

The polyorganosiloxane will typically have an average of from one to three organic substitutions per silicon atom. Representative organic substituents include saturated and unsaturated monovalent aliphatic radicals, monovalent halohydrocarbon radicals and aryl radicals.

A polyorganosiloxane frequently used in the preparation of siloxane elastomers is poly-3,3,3-trifluoropropylmethylsiloxane. Elastomers made from this fluorinated siloxane exhibit unique swelling characteristics in many solvents and oils. This siloxane can be modified with vinyl substituents which will allow it to cure according to the previously described addition reaction.

Crossliners having an ≡SiH function and previously used to cure polyorganosiloxanes having unsaturated aliphatic functions include mixtures of the following:

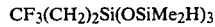

and

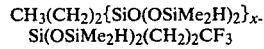

wherein x is equal to 1 or 2 and Me represents methyl.

In most instances, these compounds react and cure satisfactorily, but there are some problems. For example $CF_3(CH_2)_2Si(OSiMe_2H)_3$ is more volatile than desired. Furthermore, these compounds are most easily made from the hydrolysis and condensation of silanes such as $Me_2HSiCl$ and $CF_3(CH_2)_2SiCl_3$, and the products suffer from a lack of reproduceability.

SUMMARY OF THE INVENTION

Efforts to overcome the shortcomings enumerated above, resulted in compounds having the following formula:

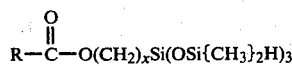

wherein R is selected from the group consisting of alkyl, having 1 to 4 carbon atoms, trifluoromethyl and phenyl, and x is an integer of 2 to 4.

DESCRIPTION OF THE PREFERRED EMBODIMENTS

This invention finds particular application in a curing system for polyorganosiloxane compositions involving the addition of an organosiloxane polymer containing aliphatic unsaturation to a compound containing silicon-bonded hydrogen atoms. The preferred organosiloxane polymers include polymers wherein at least two of the silicon atoms have attached radicals containing aliphatic unsaturation such as vinyl, allyl, methallyl, butadienyl, cyclohexenyl and vinylphenyl. From considerations of commercial availability, the preferred unsaturated radicals are vinyl radicals.

The organic radicals present in the organosiloxane polymer, in addition to the radicals containing the required aliphatic unsaturation, can be selected from monovalent hydrocarbon and substituted hydrocarbon radicals free of aliphatic unsaturation. Examples of such monovalent radicals include alkyl radicals such as methyl, ethyl, propyl, butyl, and octadecyl; cycloalkyl radicals such as cyclopentyl and cyclohexyl; aryl radicals such as phenyl and tolyl; aralkyl radicals such as benzyl and 2-phenylethyl radicals. Substituted hydrocarbon radicals include halohydrocarbon radicals such as chlorophenyl, bromomethyl and 3,3,3-trifluoropropyl radicals and cyanoalkyl radicals.

The most preferred organosiloxane polymers are the diorganopolysiloxanes wherein the organic radicals present, in addition to the radicals containing aliphatic unsaturation are selected from methyl, phenyl, and 3,3,3-trifluoropropyl radicals, at least 50 percent of the total radicals being methyl.

Examples of the polymers preferred for use with the compounds of this invention therefore include polymers composed of dimethylsiloxane units, methyl phenyl siloxane units, methyl trifluoropropyl siloxane units, methyl vinyl siloxane units and phenyl vinyl siloxane units. Preferred endblocking units would include dimethyl vinyl siloxane units, methyl diphenyl siloxane units, trimethyl siloxane units and methyl phenyl vinyl siloxane units. Any combination of these siloxane units, with the proviso that each polymer contain units with aliphatic unsaturation, would provide polymers suitable for curing with compounds of the present invention.

A wide variety of catalysts are known for promoting the addition of unsaturated compounds and compounds containing silicon bonded hydrogen atoms and any of these can be employed in conjunction with the compounds of the present invention.

Typical of such catalysts are metallic platinum, platinum deposited on supports such as charcoal or alumina, ruthenium, rhodium, palladium, iridium, salts of the platinum metals including platinic chloride, chloroplatinic acid, and complexes obtained by reacting platinum compounds with unsaturated compounds such as cyclohexene.

For any of the particular catalysts selected, the practitioner will be able to determine an optimum catalytically effective amount and conditions to promote the reaction. Platinum catalysts have been used effectively in amounts sufficient to provide from about 0.1 to 40 parts of platinum per million parts of the total reaction mixture. The particular platinum catalyst described in Example I of U.S. Pat. No. 3,419,593, issued Dec. 31, 1968 to Willing, is particularly effective with the compounds of the present invention when employed so as to provide between 2 and 20 parts of the platinum atom per million parts of the total reaction mixture. However, it has also been observed that so long as there is sufficient platinum present to exert the desired catalytic effect, the proportion employed is not narrowly criticial and proportions less than 2 and greater than 50 parts per million can be suitable in some instances.

According to the present invention, organosilicon compounds containing silicon-bonded hydrogen atoms will have the following formula:

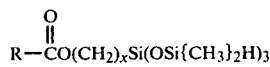

wherein R and x are as defined above. Such compounds can be prepared by reacting a compound having the formula

wherein R and x are as defined above with an excess of trichlorosilane (HSiCl$_3$) to form the corresponding silane,

The silane can then be reacted with the siloxane, {(CH$_3$)$_2$HSi}$_2$O, to form the desired compound.

The following examples will specifically illustrate the preparation of a compound within the scope of the present invention and demonstrate its utility as a cross-linker in the preparation of an elastomer.

EXAMPLE I 3-acetoxypropyltrisdimethylsiloxysilane

To 150 g (1.5 moles) of allyl acetate was added 66 ppm of platinum in the form of a divinyltetramethyldisiloxane complex of H$_2$Pt$_2$Cl$_2$.6H$_2$O as described in the Willing patent, supra. The mixture was heated to 75° C. in an oil bath and 234 g (1.65 moles, 10% excess) of HSiCl$_3$ were added slowly to keep the reaction temperature below 95° C. The resulting chlorosilane

was purified by vacuum distillation at 105°–106° C. under 6 mm Hg. The yield was about 70%.

To 252 g (1.88 moles) of {(CH$_3$)$_2$HSi}$_2$O was added 10 g of A-27 Amberlyst catalyst, a macroreticular anion exchange resin with —N(CH$_3$)$_3$+Cl− functionality (available from Rohm and Haas, Philadelphia, Pa. 19105). Prior to use the resin was washed twice with methanol and vacuum dried at 50° C. to remove moisture. Then 148 g (0.63 moles) of the

prepared above was added slowly and the reaction temperature kept below 40° C. After the addition, the mixture was heated to reflux for one-half hour. Gas liquid chromatography indicated essentially 100% conversion to 3-acetoxypropyltrisdimethylsiloxysilane. The acidity was removed by washing twice with 1500 ml aliquots of distilled water at 55° C. The silane layer was collected and dried with 8-mesh particle size anhydrous calcium sulfate. The mixture was then vacuum distilled at 89°–90° C. under 0.25 mm Hg, and a 90% yield of 3-acetoxypropyltrisdimethylsiloxysilane was obtained.

Other compounds within the scope of the present invention can be prepared according to the method of Example 1 by substituting other reactive ingredients for the allyl acetate. For example, allyl benzoate or allyl trifluoroacetate can be employed in Example 1 in place of the allyl acetate.

EXAMPLE 2

The utility of the compounds defined by the present invention as cross-linking agents was demonstrated by adding 1.5 parts by weight of 3-acetoxypropyltrisdimethylsiloxysilane to a formulation containing:

| | |
|---|---|
| vinyldimethylsiloxy endblocked poly-3,3,3-trifluoropropylmethyl siloxane having 0.27 wt. % vinyl | 100 parts by weight |
| silica filler | 20 parts by weight |
| carbon black | 1 part by weight |
| ZnO | 1 part by weight |
| platinum catalyst containing 0.6 wt. % platinum | 0.25 parts by weight. |

Specifically, the formulation was prepared by mixing 100 grams of vinyldimethylsiloxy endblocked poly-3,3,3-trifluoropropylmethylsiloxane with 0.25 grams of platinum catalyst prepared according to the method described in Example I of the Willing patent, supra. The silica filler (20 grams), carbon black (1 gram), and ZnO (1 gram), were then added and milled to give a homogenous base. 3-acetoxypropyltrisdimethylsiloxysilane (1.5 grams) was mixed into the base, milled and de-aired before being press cured at 150° C. for 60 minutes. The resulting elastomer gave the following physical properties:

| | |
|---|---|
| tensile at break | 660 psi (4.55 MPa) |
| elongation at break | 240% |
| tear (Die B) | 48 pli (8.406 × 10$^5$ N/m) |
| durometer (Shore A) | 41. |

That which is claimed is:

1. A method of curing polyorganosiloxanes wherein at least two of the silicon atoms have attached radicals containing aliphatic unsaturation said method comprising: reacting said polyorganosiloxane in the presence of a catalyst with a compound having the formula:

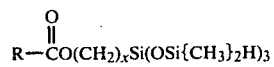

wherein R is selected from the group consisting of alkyl having 1 to 4 carbon atoms, trifluoromethyl and phenyl, and x is an integer of 2 to 4.

2. The method according to claim 1 wherein the compound is 3-acetoxypropyltrisdimethylsiloxysilane.

3. The method according to claim 1 wherein the polyorganosiloxane is vinyldimethylsiloxy endblocked poly-3,3,3-trifluoropropylmethylsiloxane.

4. The method according to claim 1 wherein the catalyst is a platinum complex.

* * * * *